(12) United States Patent
Martin

(10) Patent No.: US 9,271,714 B2
(45) Date of Patent: Mar. 1, 2016

(54) METHODS AND DEVICES FOR ANCHORING SUTURE IN BONE

(75) Inventor: Daniel Martin, Palo Alto, CA (US)

(73) Assignee: SYNTORR, INC., Palo Alto, CA (US)

( * ) Notice: Subject to any disclaimer, the term of this patent is extended or adjusted under 35 U.S.C. 154(b) by 993 days.

(21) Appl. No.: 13/011,858

(22) Filed: Jan. 21, 2011

(65) Prior Publication Data

US 2012/0191134 A1    Jul. 26, 2012

(51) Int. Cl.
*A61B 17/04* (2006.01)

(52) U.S. Cl.
CPC ......... *A61B 17/0401* (2013.01); *A61B 17/0482* (2013.01); *A61B 2017/0409* (2013.01); *A61B 2017/0414* (2013.01); *A61B 2017/0417* (2013.01); *A61B 2017/0427* (2013.01); *A61B 2017/0461* (2013.01); *A61B 2017/0496* (2013.01)

(58) Field of Classification Search
CPC ............... A61B 17/0401; A61B 2017/0412; A61B 2017/0459; A61B 2017/0409
USPC .............................. 606/232, 72, 73
See application file for complete search history.

(56) References Cited

U.S. PATENT DOCUMENTS

| 5,527,342 | A | * | 6/1996 | Pietrzak et al. | 606/232 |
| 5,683,418 | A | * | 11/1997 | Luscombe et al. | 606/232 |
| 6,096,060 | A | * | 8/2000 | Fitts et al. | 606/232 |
| 2004/0243178 | A1 | * | 12/2004 | Haut et al. | 606/232 |
| 2004/0254580 | A1 | * | 12/2004 | Boock et al. | 606/73 |
| 2005/0075636 | A1 | * | 4/2005 | Gotzen | 606/72 |
| 2005/0288682 | A1 | * | 12/2005 | Howe | 606/104 |
| 2007/0225719 | A1 | * | 9/2007 | Stone et al. | 606/72 |
| 2008/0114399 | A1 | * | 5/2008 | Bonutti | 606/232 |
| 2008/0269743 | A1 | * | 10/2008 | McNamara et al. | 606/60 |
| 2009/0088797 | A1 | * | 4/2009 | Crombie et al. | 606/232 |
| 2010/0004683 | A1 | * | 1/2010 | Hoof et al. | 606/232 |
| 2010/0016892 | A1 | * | 1/2010 | Kaiser et al. | 606/232 |
| 2010/0036416 | A1 | * | 2/2010 | Martin | 606/232 |
| 2010/0217318 | A9 | * | 8/2010 | Bartlett et al. | 606/232 |
| 2010/0222812 | A1 | * | 9/2010 | Stone et al. | 606/232 |
| 2010/0292731 | A1 | * | 11/2010 | Gittings et al. | 606/232 |
| 2010/0292733 | A1 | * | 11/2010 | Hendricksen et al. | 606/232 |

FOREIGN PATENT DOCUMENTS

| EP | 1484022 A2 | 12/2004 |
| EP | 1690499 A2 | 8/2006 |
| EP | 1862127 A1 | 12/2007 |

OTHER PUBLICATIONS

European Search Report dated May 15, 2015 in counterpart European Patent Application 12736494.1-1654 / 2665427 PCT/US2012021891.

* cited by examiner

*Primary Examiner* — Gregory Anderson
*Assistant Examiner* — Christina Lauer
(74) *Attorney, Agent, or Firm* — Patterson & Sheridan, LLP

(57) ABSTRACT

An elongate rigid suture anchor is provided which is driven and impacted directly into bone. It has two ends: a distal end, which forms a hole in the bone, and a proximal end that penetrates the sidewall of the bone hole as the anchor is displaced proximally in the hole. A proximal force is applied to the suture anchor to displace the anchor proximally and cause tilting of the anchor. As the anchor is displaced proximally, the proximal end of the anchor enters obliquely into the sidewall of the hole.

13 Claims, 7 Drawing Sheets

METHODS AND DEVICES FOR ANCHORING SUTURE IN BONE

BACKGROUND

Suture anchors are used to anchor suture in various medical procedures such as glenoid labrum and rotator cuff surgery. The suture anchor is anchored into bone and one or more sutures are coupled to the suture anchor to hold the sutures in their intended position.

The present invention is directed to new methods and devices for anchoring sutures in bone.

SUMMARY

In one aspect of the present invention, a suture anchor is provided which has a sharp distal end that forms the tip of the suture anchor assembly. The sharp distal end of the suture anchor is driven into bone directly to form a hole in the bone. As such, the suture anchor itself may act like a bone punch or a bone drill, which obviates the need for a separate device in a number of aspects of the present invention. The suture anchor is mounted to an introducer and is released once the suture anchor has been driven to the desired depth. The introducer is then withdrawn leaving the anchor impacted in the depth of the hole as further described below. Traction is then applied to the suture causing the anchor to move proximal in the hole and tilt. The tilting causes both the proximal and distal ends to engage the sidewall of the hole on opposing sides of the hole. Sidewall engagement holds the anchor in the hole. The pull-out resistance of the anchor in the hole is provided primarily by penetration of the proximal end into the sidewall in one aspect of the invention. Since the proximal end acts like a "spike" in the bone, the anchor may not have to be "tilted" as much as prior art anchors, which typically tilt 90 degrees, and may tilt less than 45 degrees.

In another aspect of the invention, the proximal end of the suture anchor penetrates the sidewall of the hole further than the distal end penetrates the sidewall. Many conventional suture anchors attempt to anchor tilting-type anchors with both ends penetrating the sidewall of the hole about the same amount. The proximal end of the suture anchor may be driven into the sidewall of the hole so that at least half of a length of the suture anchor is driven into the sidewall along a side of the suture anchor. Stated another way, the suture anchor is driven into the sidewall so that at least part of a midsection of the anchor penetrates the sidewall with the midsection being a transverse plane lying halfway between the proximal and distal ends. While the proximal end may be preferentially driven into the bone, the distal end may not penetrate bone as much as the proximal end. Stated still another way, the proximal end may penetrate the bone a transverse distance which is at least three times larger than a transverse distance that the distal portion penetrates bone. In still another aspect of the present invention, a distance (measured along the longitudinal axis of the anchor), which the proximal end is driven into bone is at least three times larger than a distance (also measured along the longitudinal axis of the anchor) that the distal end is driven into bone.

In still another aspect of the present invention, the suture anchor may be formed in relatively small sizes so that the maximum outer transverse dimension of the anchor is no more than four times the nominal USP diameter of the suture coupled to the suture anchor Stated another way, when a plurality of sutures are attached to the anchor, the sum cross-sectional area of the sutures is at least 20% of the hole cross-sectional area (or the maximum bone anchor cross-sectional area).

These and other aspects of the present invention will become apparent from the following description of the preferred embodiments, drawings and claims The details of one or more embodiments of the invention are set forth in the accompanying drawings and the description below. Other features, objects, and advantages of the invention will be apparent from the description and drawings, and from the claims.

DETAILED DESCRIPTION

Figure 1:
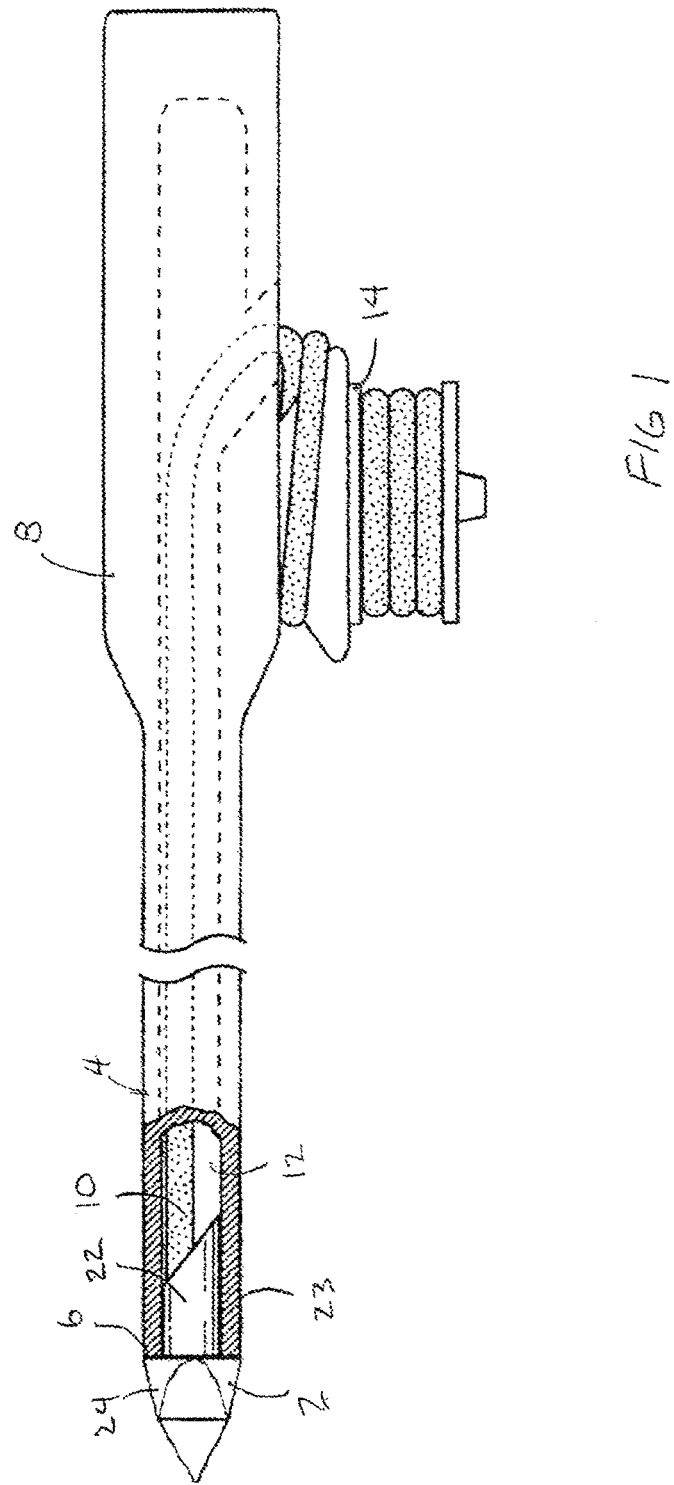
FIG. 1 shows a suture anchor mounted to an introducer.
Figure 2:
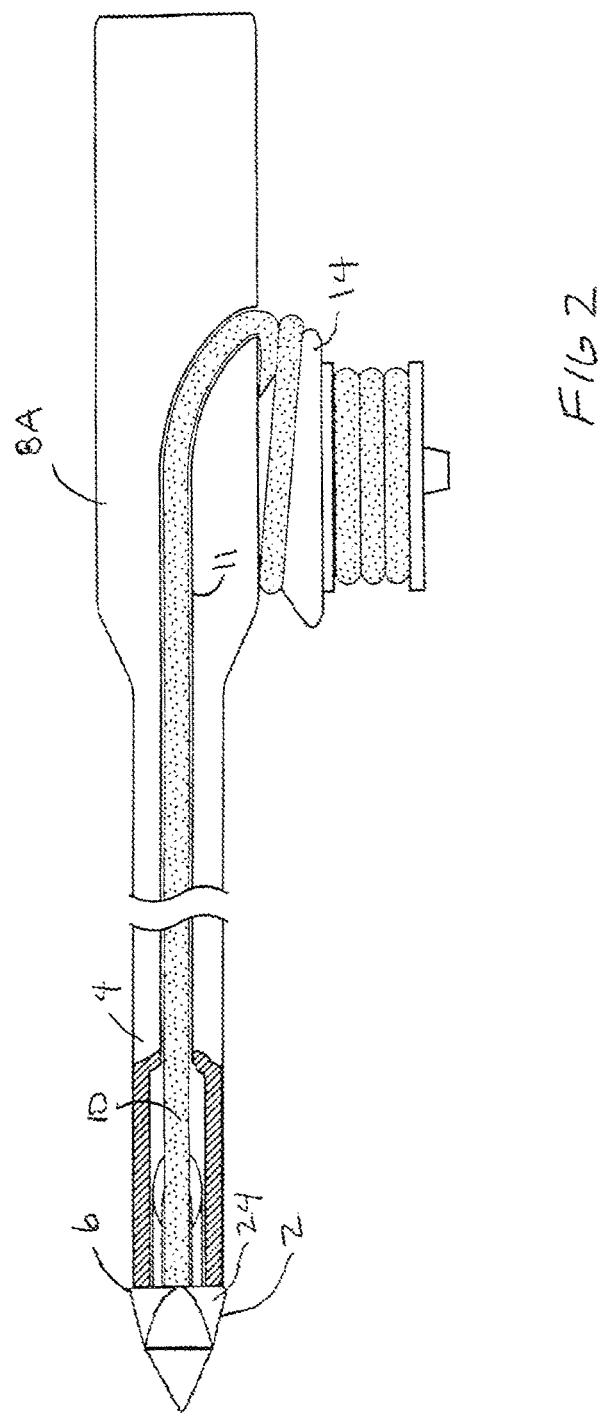
FIG. 2 shows a suture anchor mounted to another introducer.
Figure 3:
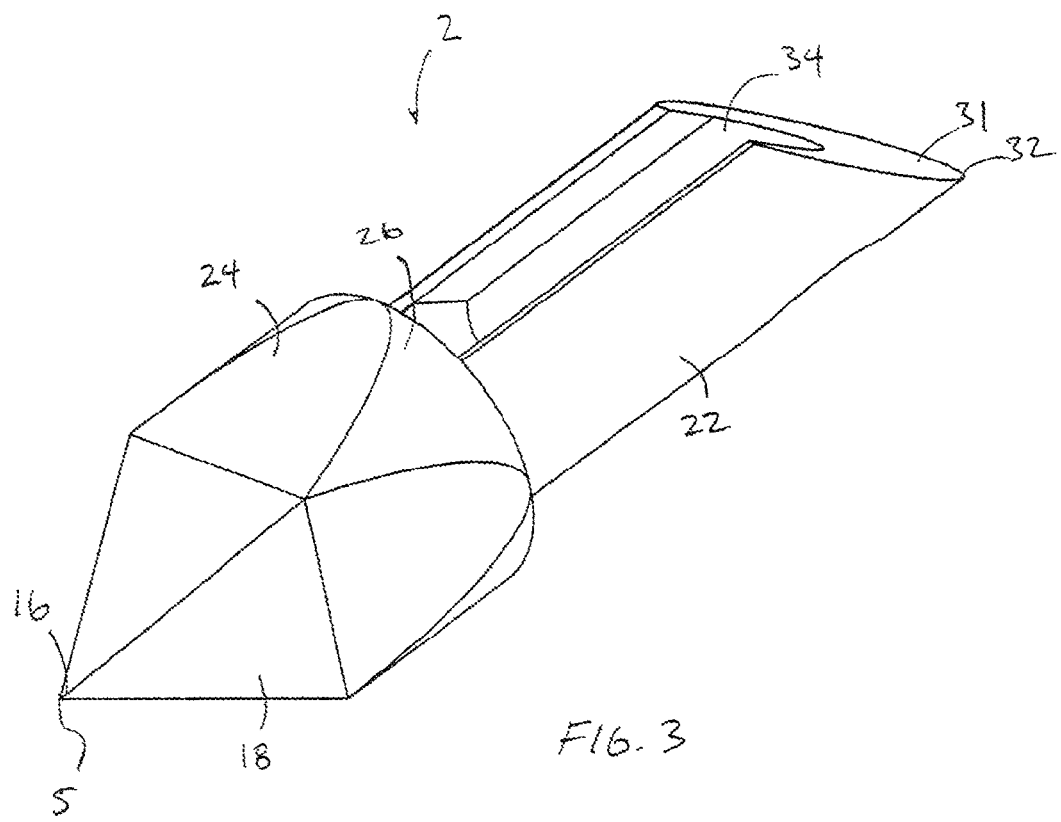
FIG. 3 shows the suture anchor.

Referring to FIGS. 1-5, a suture anchor 2 and a suture anchor delivery system 4 are shown. The suture anchor 2 is mounted to a distal end 6 of an introducer 8. One or more sutures 10 are coupled to the suture anchor 2 and extend through a lumen 12 in the introducer 8. A suture lock 14 is positioned at the proximal end of the introducer 8 to maintain tension on the suture 10. Suture tension may be used to hold the suture anchor 2 at the end of the introducer 8 as described in further detail below. The suture anchor 2 may be held at the distal end of the introducer 8 using another removable suture (not shown) or any other suitable releasable connection without departing from numerous aspects of the present the invention. The introducer 8 of FIG. 1 has a lumen (see FIG. 5), which receives the suture 10. Alternatively, another introducer 8A is shown in FIG. 2 which has a slot 11 on an exterior surface in which the suture 10 resides. The particular introducer 8, 8A is selected depending upon the particular suturing procedure which will be undertaken by the user. Use of the introducer 8 is essentially the same as use of the introducer 8A and discussion of one is equally applicable to use of the other.

The suture anchor 2 has a tip 16 at a distal end 5 so that the suture anchor 2 may be directly driven into bone. The tip 16 has four beveled sides 18 that converge to form the tip 16. A shoulder 20 contacts the distal end 6 of the introducer 8. The shoulder 20 is generally annular shaped and may have a slightly enlarged portion 22 along one side. The shoulder 20 separates the suture anchor 2 into a proximal portion 22 and a distal portion 24. The distal portion 24 gradually increases in cross-sectional area toward the shoulder 20. The suture anchor 2 may be formed from one piece of material so that the entire anchor is integrally formed or at least the portions which engage bone such as the proximal and distal ends. The suture anchor 2 may include other parts, including movable or deformable parts, without departing from this and other aspects of the invention so long as those parts are not associated with bone engagement in this aspect of the invention. For example, these parts may be associated with suture locking or release of the anchor from the introducer 8 rather than engaging bone. The suture anchor 2 may be made of any suitable material such as metal, ceramic or a high strength plastic. Of course, numerous aspects of the invention may be practiced with the suture anchor 2 being made of numerous parts which may or may not be movable or deformable and which may or may not engage bone.

The anchor 2 is driven directly into bone as will be described in further detail below. The anchor 2 itself forms the distal end of the device so that the anchor 2 forms the tip of a driver 23 which may act like a bone drill or serves as a bone punch. As such, the delivery system 4 is simplified since the anchor 2 itself forms the penetrating tip of the driver 23. Many other prior art anchors are delivered into a pre-drilled hole or are contained within the bone-hole forming instruments, rather than forming the tip of the driver 23 itself. The anchor 2 is driven directly into bone from the surface of the bone to the desired depth. The anchor 2 is then released by simply releasing the suture lock 14 and withdrawing the introducer 8 as described below. The distal portion 24 does not include a threaded exterior surface although various aspects of the present invention may be practiced with the distal portion 24 having a threaded exterior surface. Some conventional suture anchors are rotated into threaded engagement with the bone which may prevent the suture anchor from having the ability to be withdrawn within the hole in the manner that the suture anchor 2 can be withdrawn as explained herein.

The distal portion 24 of the anchor 2 is designed to become impacted at the bottom of the driven hole. To this end, the anchor 2 has an outer surface 26 that may form the largest transverse outer dimension of the anchor 2 and the introducer 8. The outer surface 26 may be sized larger than the introducer 8 to facilitate withdrawal of the introducer 8. When the anchor 2 is driven into bone, the outer surface 26 of the anchor 2 is impacted at the bottom of the hole so that the anchor 2 is frictionally engaged and held by the sides of the hole created by the anchor 2. The outer surface 26 is shown formed in four discrete parts but may, of course, be a single continuous surface or may be formed with more or fewer than four parts. The outer surface 26 may also be a formed in any other manner such as two relatively small areas on opposite sides of the anchor so long as the opposing surfaces form the largest outer dimension of the anchor 2. The frictional engagement between the bottom of the hole and the outer surface 26 holds the anchor 2 so that the suture 10 must be pulled with a reasonable force to overcome this frictional engagement and catching of the edge of the shoulder 20 as described below in connection with use of the anchor 2. Prior art anchors which are advanced into a pre-drilled hole differ from this aspect of the present invention since such anchors sit loosely at the bottom of the hole rather than being impacted against the sides of the hole, and therefore require a special supplemental mechanism for deployment from the introducer tool or to initiate tilting of the anchor. As will be described above, the present invention may also be practiced without deformable or movable mechanisms or barbs that engage bone which many prior art anchors require.

Figure 4:
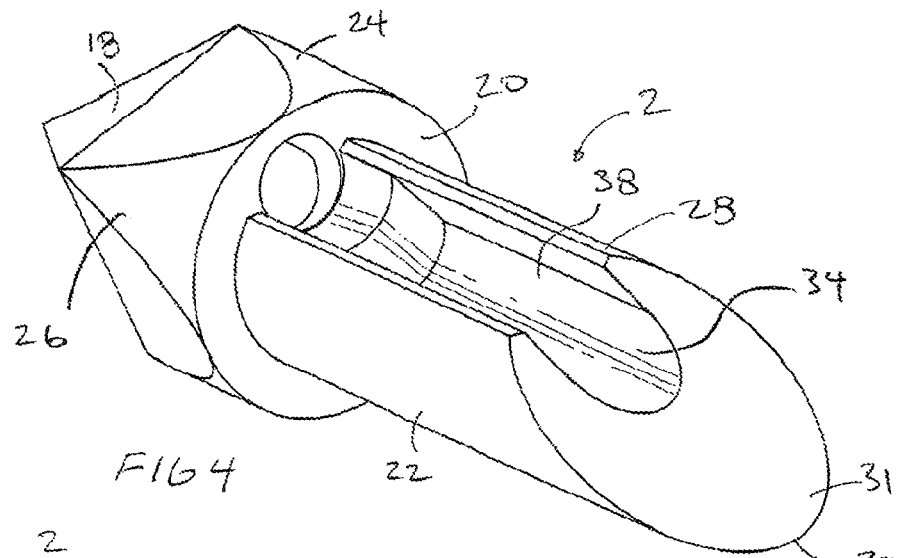
FIG. 4 shows another view of the suture anchor.
Figure 5:
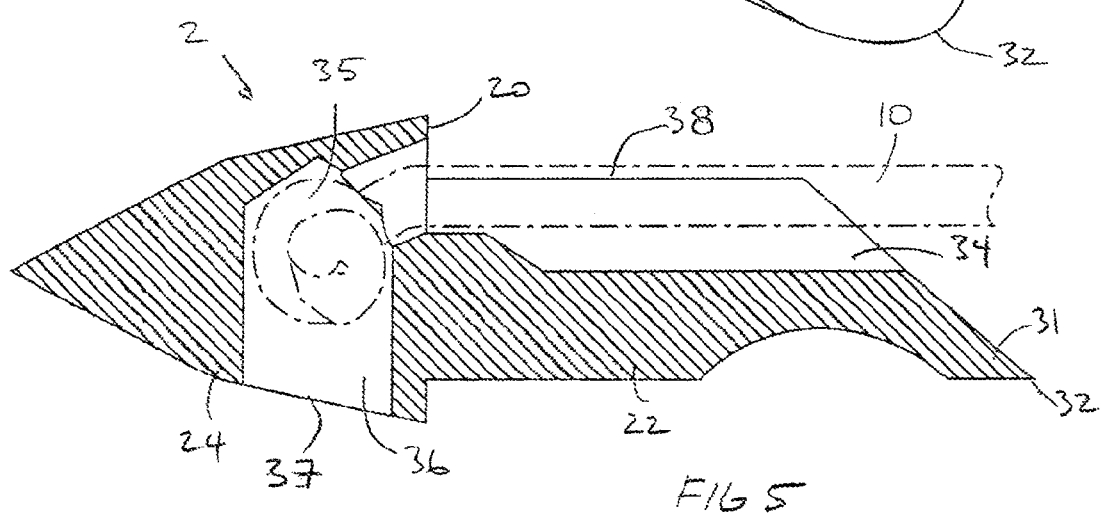
FIG. 5 is a cross-sectional view of the suture anchor.

The proximal portion of the suture anchor 2 extends proximally from the shoulder 20 and may include a keyed portion 28 having an exterior surface 30 that matches an interior surface of the introducer 8 so that torque may be transmitted from the introducer 8 to the suture anchor 2. The keyed portion may be a multi-faceted portion or may take any other suitable shape, such as oval as shown in FIG. 4, without departing from the scope of the invention. Of course, the keyed portion 28 may not be required if the anchor 2 is simply driven directly into the bone without rotation.

Figure 6:
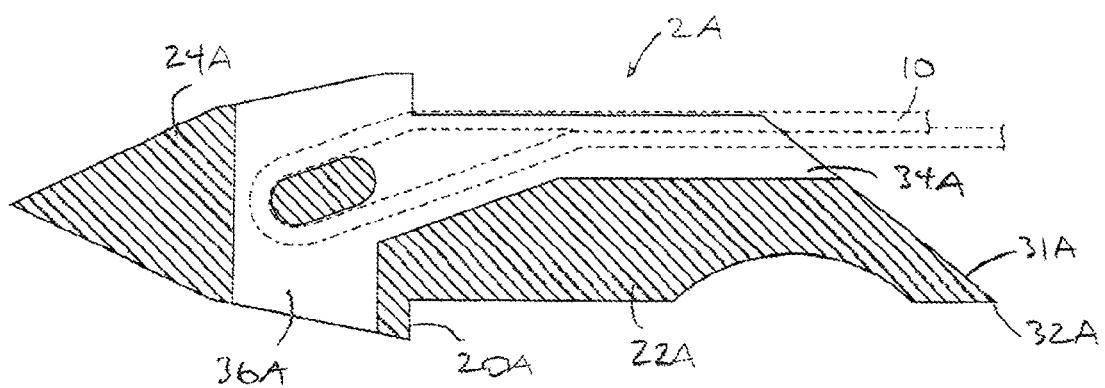
FIG. 6 is a cross-sectional view of another suture anchor.

A proximal end 31 of the suture anchor 2 also has a sharp tip 32 to penetrate bone as described in greater detail below. One or more suture channels 34 may extend through the proximal portion and communicate with a recess 36 in the distal portion of the anchor 2. The suture channel 34 includes a slot 38 on one side, which permits the suture 10 to enter and leave the channel 34. Alternatively, the suture 10 when passing along the proximal portion may reside partially or completely in a slot or groove in the most distal portion of the introducer, before proceeding proximally either into the lumen of the introducer or to a continuation of a slot on the side of the introducer without departing from the scope of the invention. A knot 35 may be formed in the suture 10, or other enlargement 11 on to the suture such as a metallic or polymer bead, clip, crimp, or other such attachment, to secure the suture 10 to the anchor 2. The knot 35 is positioned in the recess 36 with the ends of the suture 10 extending through the suture channel 34 and into the lumen 12 of the introducer 8. An opening 37 in the distal portion 24 is in communication with the recess 36 so that the suture 10 may be manipulated to secure the suture anchor 2 to the suture 10 or to secure and position the enlargement 11 onto the suture 10 and into the recess 36. The suture channel 34 may be positioned off-set relative to the center of gravity or geometric central axis CA (see FIG. 7) of the anchor 2 and the introducer 8 for the reasons described below in connection with use of the anchor 2. Alternatively, the recess 36 may be swaged, welded or glued to prevent removal of the suture 10 from the recess 36 with or without the knot 35. Referring to FIG. 6, another suture anchor 2A is shown wherein the same or similar reference numbers refer to the same or similar structure and all uses of the suture anchor 2 or suture anchor 2A are equally applicable to the other. The recess 36A may also include a curvilinear passage, which receives a sliding loop of the suture 10 with both ends passing through the suture channel 34 and proximally into control of the user. Alternatively, the anchor 2 may include a mechanism that permits unidirectional sliding of one or more sutures 10. Such a mechanism may include movable or deformable parts that engage the suture 10 but are not intended to engage bone.

Figures 7, 8:
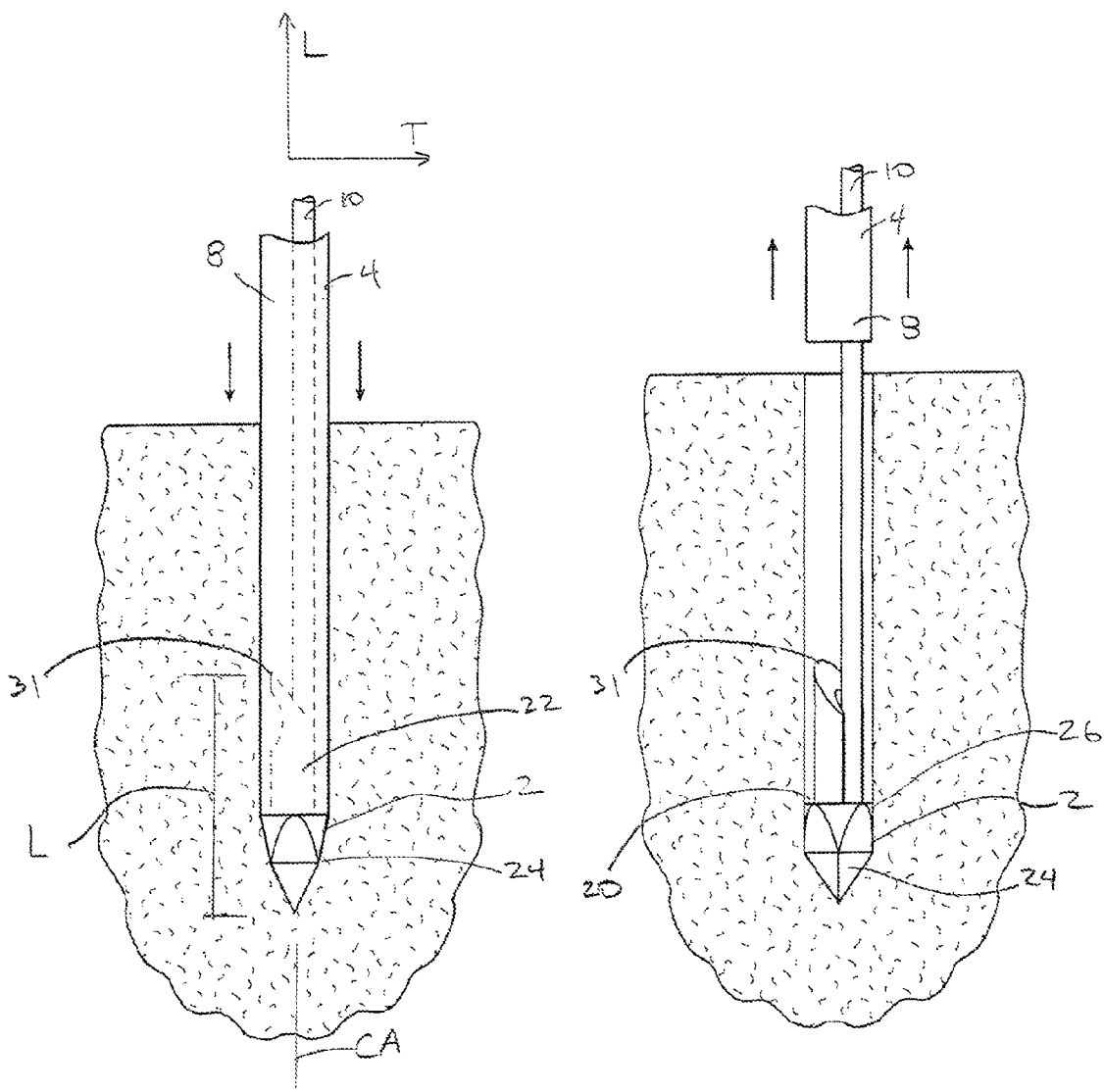
FIG. 7 shows the suture anchor driven into bone to form a hole.
FIG. 8 shows the introducer removed and the view rotated 45 degrees relative to FIG. 7.

Use of the suture anchor 2 is now described with reference to FIGS. 7-11. The suture anchor 2 is driven directly into bone from the surface of the bone to form a hole in the bone. The introducer 8 may be rotated during driving of the suture anchor 2 to aid in advancing the anchor 2 into bone. The suture anchor 2 may also be driven into a pilot hole that is smaller or less deep than full insertion depth or width without departing from numerous aspects of the present invention. The pilot hole is sized smaller than the outer surface 26 of the anchor 2 so that the anchor 2 is still being driven into the bone to create the full transverse dimension of the hole H where it resides and so that the anchor 2 is impacted at the bottom of the hole. The hole in which the suture anchor 2 is positioned defines a longitudinal direction L and a transverse direction T that will now be used to described aspects of the present invention. Once the suture anchor 2 has been driven to the desired depth, tension on the sutures is released by releasing the suture lock 14 (see FIG. 1). Releasing tension on the suture 10 releases the suture anchor 2 from the introducer 8. The suture anchor 2 may be coupled to the introducer 8 in any other fashion such as a second suture or a releasable connection such as a threaded connection between the suture anchor 2 and introducer 8. The introducer 8 may then be removed leaving the suture anchor 2 and the sutures 10 within the hole as shown in FIG. 8. The anchor 2 is held at the bottom of the hole by frictional engagement between the anchor 2 and the sidewall of the hole. No supplemental mechanism or component may be required to uncouple or expel the anchor from the end of the introducer although one may be provided without departing from numerous other aspects of the present invention. The anchor 2 also does not require a stiffened suture or stiff metallic cable to uncouple or expel the anchor from the introducer 8 although, again, one may be provided without departing from the invention. The anchor 2 sits within the hole without any engagement or contact of the proximal end 31 of the anchor 2 with the sidewall of the hole.

Figures 9, 10:
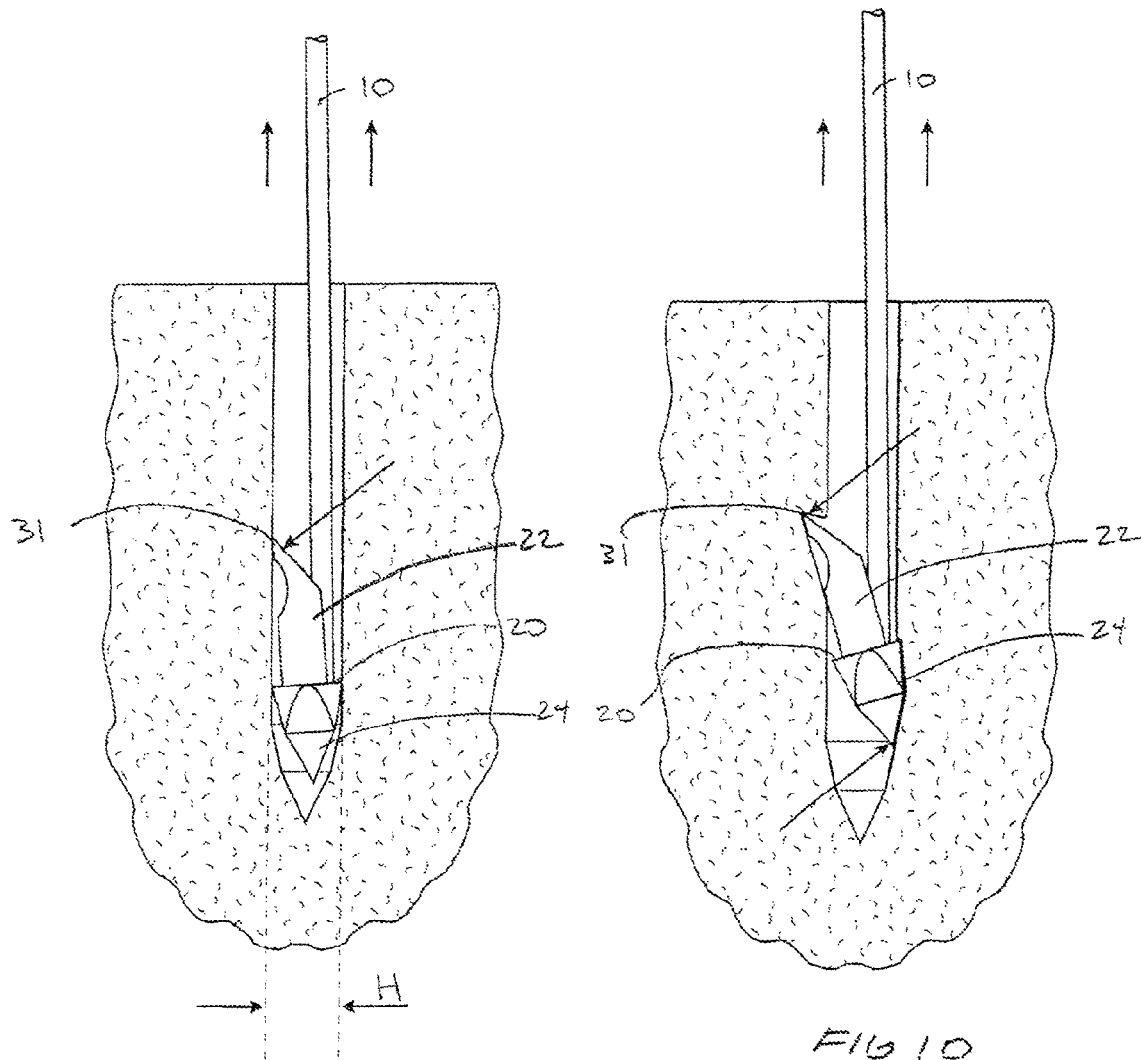
FIG. 9 shows the suture anchor moved proximally within the hole until the proximal end contacts the sidewall of the hole.
FIG. 10 shows the suture anchor displaced proximally within the hole so that the proximal end penetrates the sidewall of the hole and begins tilting.

The suture or sutures 10 are then tensioned to produce a force on the suture anchor 2 that tends to move the anchor 2 proximally within the hole. When tension is initially applied to the suture 10, the anchor 2 resists movement due to the fact that the anchor 2 is impacted at the bottom of the hole. Upon application of sufficient tension on the suture 10, the frictional force holding the suture anchor 2 caused by impaction, and scraping of the corner of the shoulder 20, is overcome and the suture anchor 2 moves proximally within the hole. The initial proximal movement occurs with tilting until the proximal end of the suture anchor 2 contacts the sidewall of the hole as shown in FIG. 9. Continued tension on the suture 10 causes the proximal end 31 (and the distal end to a lesser extent) to penetrate the sidewall of the hole. The anchor 2 advantageously may not require movable or deformable parts to engage the wall of the hole which makes for a simpler assembly than some prior art anchors which require deformable or actuated barbs or the like to engage the hole prior to or in association with proximal movement of the anchor 2. The anchor 2 also does not require an insertion shaft, which is pushed against the anchor to deform the anchor 2 or to move the proximal end 31 of the anchor 2 into engagement with the wall of the hole, or is elastically bent to bias a portion of the anchor against the sidewall, or holds a proximal corner of the anchor against the sidewall during insertion. The anchor 2 also does not have and does not require an elastic connection or cable that will bias the anchor into a tilted position as soon as the anchor becomes separated from the introducer. The anchor 2 relies on the frictional engagement between the anchor 2 and the hole to initially resist the proximal force applied to the anchor by the suture 10. As mentioned above, the suture channel 34 (see FIGS. 3-6) may be eccentrically positioned relative to the central axis CA (see FIG. 7) of the anchor 2 and the introducer 8 so that suture tension causes a moment to be applied to the suture anchor 2, which causes the anchor 2 to tilt within the hole, in association with proximal displacement, as shown in FIG. 9. Once the suture anchor 2 has tilted within the hole, the distal portion 24 may also penetrate the sidewall somewhat but much less than the proximal end. The distal portion 24 is relatively large compared to the proximal portion 22 so that the distal portion 24 does not easily penetrate bone when tension is applied to the sutures 10. The present invention has been described without use of a pusher to release the anchor or initiate tilting, however, numerous aspects of the present invention may be practiced with a pusher or insertion shaft without departing from the scope of the invention. A portion 35 of the shoulder 20 may penetrate the sidewall of the hole on the same side of the hole as the proximal end 31 of the anchor 2 and may serve as somewhat of a "stop" as the proximal end 31 is driven into the sidewall (see FIG. 11).

Figure 11:
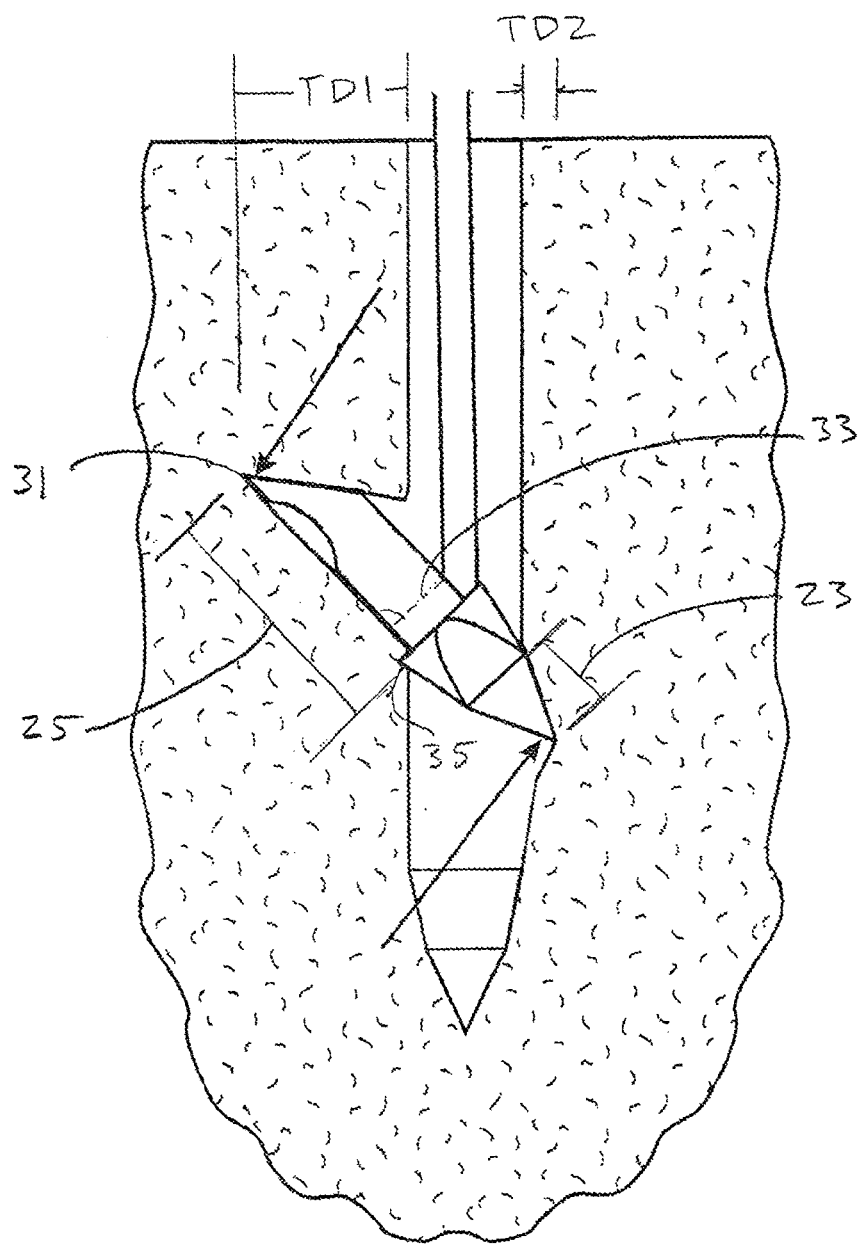
FIG. 11 shows the suture anchor tilted further.

The proximal end 31 of the suture anchor 2 is driven into the bone like a "spike" which differs from many conventional anchors, which attempt to anchor both ends into bone somewhat equally rather than primarily the proximal end. The proximal end may tilt at an angle of less than 45°, which also differs from many conventional anchors that generally are tilted about 90 degrees. The proximal end 31 may be driven into the sidewall of the hole so that at least half of a length L (see FIG. 7) of the suture anchor 2 penetrates or intersects with the sidewall on at least one side of the suture anchor 2 as shown in FIG. 11. Stated another way, the suture anchor 2 is driven into the sidewall so that at least part of a midsection 33 penetrates or intersects the sidewall. The midsection 33 is a transverse cross section, which lies halfway between the proximal and distal ends. Stated still another way, the suture anchor 2 is driven into the sidewall a distance TD1 that is equal to at least half the length L of the suture anchor 2. While the proximal end 31 is preferentially driven into the bone, the distal portion 24 does not penetrate bone as much as the proximal portion 22 due to the larger cross-sectional size of the distal portion, and the larger surface area that presents against the sidewall. As such, the proximal portion 22 may penetrate the bone with the transverse distance TD1 being at least three times larger than a transverse distance TD2 that the distal portion 24 penetrates bone. In still another aspect of the present invention, a distance 23 (measured along the longitudinal axis of the anchor 2) which the proximal end 31 is driven into bone is at least three times larger than a distance 25 (also measured along the longitudinal axis of the anchor 2) that the distal end is driven into bone. As mentioned below, the proximal and distal ends 22, 24 may in some circumstances, such as low bone density, penetrate the bone in a relatively equal manner without departing from other aspects of the present invention.

The suture anchor 2 displaces by design farther proximally in its hole, in the course of finding anchorage in bone, than do many other suture anchors. The proximal displacement is relative to the insertion hole transverse diameter. In other anchors that have their locking mechanisms biased against the sidewall with elastic or insertion-tools, or by notches in the sidewall, immediate engagement with the side-wall is made, preventing the anchor from displacing proximally in the hole. The suture anchor 2 may function somewhat differently in that the anchor may slide against the sidewall with the anchor 2 sliding at least one hole diameter and may even slide at least two hole diameters in some aspects of the invention. The suture anchor 2 may tilt at an angle of less than 45°, and may tilt as little as shown in FIG. 10 when in hard bone, although greater tilting may be accomplished without departing from the invention. With progressive sliding and penetration, the angle of penetration increases, as does the resistance to continued sliding and tilting.

The suture anchor 2 of the present invention may also be formed in relatively small sizes so that the outer surface 26, which represents the maximum outer transverse dimension of the anchor 2, is no more than 0.080 inch and may be, for example, about 0.062 inch. Stated another way, the suture anchor 2 may have a maximum outer transverse dimension (which is the outer surface in the preferred embodiment) that is no more than four times the nominal USP diameter of the suture 10. This small size is made possible because the design may be a single piece fabrication without moveable parts or elastic elements, and thus can be made in small sizes.

The suture anchor 2 has special characteristics that allow the use of relatively large sutures attached to the anchor 2. The design makes possible using attached sutures with nominal sum total cross sectional area of at least 20% of the anchor maximum cross sectional area when a plurality of sutures are coupled to the suture anchor. The anchor maximum cross sectional area is generally represented by a disc having a diameter equal to transverse dimension of the distal portion adjacent to the shoulder. As an example, an anchor of 0.063 inch transverse dimension can accommodate a double strand of USP No. 2 suture, USP No. 2 suture having a nominal diameter of 0.020 inch.

Having relatively large sutures attached to the anchor is beneficial to clinical application because a relatively small transverse dimension suture anchor may be affixed to a strong and thick suture. The small entry hole of the suture anchor inflicts less volume damage on the bone, and allows closer proximity of multiple anchors. The thicker suture is generally stronger and is less inclined to cut through the soft tissue structures being repaired.

Integration of multiple aspects of the invention makes the use of relatively large suture size and small suture anchor possible. The suture recess 36 is positioned in the distal portion, where there is sufficient space to accommodate the enlargement 11 on the suture. The suture channel 36 in the proximal portion allows passage of large sutures within the introducer adjacent to the proximal portion. A deployment tool is absent in the introducer lumen, making space for large sutures compared to some anchors, which require a deployment mechanism or tool. Absence of a deployment tool also allows for greater material cross section of the introducer, allowing the introducer to deliver the forces necessary for driving the anchor into bone without pre-drilling. The shape of the distal portion leads to impaction of the anchor at the conclusion of the driving step, allowing the introducer to be withdrawn away from the anchor without a supplemental deployment tool. In the slotted configuration of the introducer, the self-deploying nature of the anchor is again essential, because the slot precludes a lumen in the introducer for passage of a deployment tool. Relatively large suture size, especially in suture anchors that are self-driving, is a difference between some aspects of the present invention and many conventional anchors.

The differential sizes and shapes of the proximal and distal portions 22, 24 of the suture anchor 2 are also an aspect of the invention. The distal portion 24 penetrates the bone to form the hole in the bone while the proximal portion 22 penetrates the sidewall of the hole that is formed. The transverse dimension of the distal portion 24 forms a bone hole having the same transverse dimension as the distal portion so that the anchor 2 is impacted at the bottom of the hole. The introducer 8, on the other hand, may be slightly smaller than the hole. The impaction of the anchor 2 first functions to cause the anchor 2 to disengage out of the introducer 8 upon withdrawal of the introducer 8 without any accessory mechanism or deployment tool. The impaction secondly causes some resistance to a traction force subsequently applied to the suture, such that tension on the suture causes a tilting moment on the anchor 2 when the suture is tensioned. The large transverse dimension and associated surface area causes the distal portion 24 to slide against the sidewall, with minimal penetration of the sidewall, as the anchor 2 is displaced retrograde in the hole. The proximal portion 22 has the sharp tip 31, presenting minimal surface area to the sidewall as it contacts the sidewall, leading to penetration of the sidewall primarily by the proximal portion 22. The onset of penetration, or catching, of the sidewall by the proximal end 31 is one aspect of the invention, because this causes the traction force on the suture to deliver a force on the proximal end 31 directed into the sidewall. This force in turn causes further penetration and tilting of the anchor 2. The proximal portion 22 is of a smaller maximum transverse dimension than the distal portion, in order that there is space for the introducer that fits over the proximal portion, the introducer being not substantially larger in transverse dimension than the distal portion. The smaller transverse dimension of the proximal portion 22 also allows tilting of the anchor 2 so that the proximal end 31 may engage and penetrate into the sidewall of the hole as the anchor 2 slides retrograde. The shoulder may be designed to make possible numerous functions of the anchor 2. The shoulder may, of course, act as the contact surface for transferring forces from the introducer 8 to the anchor 2 during advancement of the anchor 2 in bone. The shoulder may also help initiate tilting by "catching" the sidewall of the hole during initial tensioning of the suture. Finally, the shoulder may also act as a stop as the proximal end is driven into bone as described above. The shoulder critically integrates with other design elements. The surface of the shoulder may be at an angle to the anchor-axis different than 90° without departing from the invention, though 90° is consider to be an optimal angle. The taper of the distal portion also allows tilting of the anchor sufficient for the proximal tip to touch against the sidewall and begin entry into the sidewall of the hole. The smaller transverse dimension and small transverse tip cross section of the proximal portion 22 also allows penetration by the proximal portion 22 more easily than by the distal portion 24, causing a tendency to slide against the sidewall by the distal portion 24, and a tendency to penetrate the sidewall by the proximal portion 22.

The present invention has been described with reference to preferred embodiments, however, it is understood that numerous modifications could be made without departing from the scope of the invention. For example, in association with special bone morphology, both ends of the anchor may penetrate the bone equally or relatively equally without departing from aspects of the invention. The distal portion may be shaped in alternative ways to facilitate driving into bone, for example in a cone shape, or intersecting cone shapes, or with a shape having beveled sides numbering other than four, or having beveled sides each with a single slope, or as a foreshortened spade-point drill.

What is claimed is:

1. A suture anchor assembly, comprising:
    a suture anchor having a proximal end, a proximal portion that includes the proximal end, a distal end that is shaped to penetrate bone and configured to penetrate the bone to form a hole from a surface of the bone to a desired depth, and a distal portion that includes the distal end and has a shoulder that defines a distal end of the proximal portion and a proximal end of the distal portion;
    an introducer having a first end that engages with the shoulder during insertion of the suture anchor into the bone to transfer an insertion force to the suture anchor, and an interior portion in which the proximal portion of the suture anchor is entirely received while the first end is engaged with the shoulder; and
    a suture securing section in the distal portion of the suture anchor by which a force is applied to the suture anchor to cause the suture anchor to be tilted within the hole,
    wherein the proximal portion of the suture anchor has a bone engagement portion that penetrates a sidewall of the hole when the introducer is removed and the force is applied to the suture securing section to cause the suture anchor to be tilted within the hole.

2. The suture anchor assembly of claim 1, wherein:
    the suture anchor has a maximum outer transverse dimension at the distal portion and not at the proximal portion.

3. The suture anchor assembly of claim 2, wherein the distal portion has an outer surface that forms the maximum outer transverse dimension of the suture anchor.

4. The suture anchor assembly of claim 2, wherein the distal portion has a disc-shaped cross-section adjacent to the shoulder and having a diameter equal to the maximum transverse dimension of the distal portion.

5. The suture anchor assembly of claim 1, wherein:
the proximal and distal portions of the suture anchor are formed integrally from a single piece of material.

6. The suture anchor assembly of claim 1, wherein:
the suture anchor is formed so that all portions which engage bone are formed from the single piece of material.

7. The suture anchor assembly of claim 1, wherein the proximal portion of the suture anchor has a suture channel.

8. The suture anchor assembly of claim 7, wherein:
the suture channel is eccentrically positioned so that an eccentric force is applied to the suture securing section when suture positioned in the suture channel is tensioned.

9. The suture anchor assembly of claim 7, wherein:
the suture channel includes a slot, the slot permitting suture to enter and leave the suture channel.

10. The suture anchor assembly of claim 1, wherein the shoulder includes a keyed portion that is engaged with a corresponding portion on the introducer such that, when torque is applied to the introducer, the torque is transmitted to the suture anchor by way of the keyed portion to cause the distal portion to be driven into the bone while rotating.

11. The suture anchor assembly of claim 1, wherein the distal portion includes beveled sides that converge to form a point at the distal end.

12. The suture anchor assembly of claim 1, further comprising:
a suture attached to the suture securing section by which the force is applied to the suture securing section.

13. A suture anchor assembly, comprising:
a suture anchor having a distal end that has a shoulder and extends from the shoulder to a distal end of the suture anchor, and a proximal portion that extends from a proximal end of the suture anchor to the shoulder of the distal portion, wherein the distal end is shaped to penetrate bone and configured to penetrate the bone to form a hole from a surface of the bone to a desired depth;

an introducer having a first end that engages with the shoulder during insertion of the suture anchor into the bone to transfer an insertion force to the suture anchor, and an interior portion in which the proximal portion of the suture anchor is entirely received while the first end is engaged with the shoulder; and a suture securing section in the distal portion of the suture anchor by which a force is applied to the suture anchor to cause the suture anchor to be tilted within the hole, wherein the proximal portion of the suture anchor has a bone engagement portion that penetrates a sidewall of the hole when the introducer is removed and the force is applied to the suture securing section to cause the suture anchor to be tilted within the hole.

* * * * *